United States Patent
Hatahori

(10) Patent No.: US 10,288,550 B2
(45) Date of Patent: May 14, 2019

(54) FLOW CELL

(71) Applicant: SHIMADZU CORPORATION, Kyoto-shi, Kyoto (JP)

(72) Inventor: Takahide Hatahori, Kyotanabe (JP)

(73) Assignee: SHIMADZU CORPORATION, Kyoto (JP)

( * ) Notice: Subject to any disclaimer, the term of this patent is extended or adjusted under 35 U.S.C. 154(b) by 152 days.

(21) Appl. No.: 13/903,869

(22) Filed: May 28, 2013

(65) Prior Publication Data

US 2014/0055782 A1     Feb. 27, 2014

(30) Foreign Application Priority Data

Aug. 21, 2012   (JP) .................................. 2012-182535

(51) Int. Cl.
G01N 21/03 (2006.01)
G01N 21/05 (2006.01)

(52) U.S. Cl.
CPC .......... *G01N 21/0303* (2013.01); *G01N 21/05* (2013.01)

(58) Field of Classification Search
CPC ........... G01N 21/05; G01N 2021/0346; G01N 21/0303
USPC ....................................................... 356/246
See application file for complete search history.

(56) References Cited

U.S. PATENT DOCUMENTS

| | | | |
|---|---|---|---|
| 3,954,341 A * | 5/1976 | Uffenheimer | 356/246 |
| 4,477,186 A | 10/1984 | Carlson | |
| 4,781,456 A * | 11/1988 | Nogami | G01J 3/427 356/320 |
| 5,312,535 A * | 5/1994 | Waska | G01N 27/44721 204/603 |
| 6,104,485 A * | 8/2000 | Wang et al. | 356/246 |
| 6,542,231 B1 * | 4/2003 | Garrett | G01N 21/05 250/227.11 |
| 6,678,051 B2 * | 1/2004 | Gerner | G01N 21/05 356/246 |

(Continued)

FOREIGN PATENT DOCUMENTS

JP     55-060838 A     5/1980
JP      9-274013 A     10/1997

(Continued)

OTHER PUBLICATIONS

National Physical Laboratory, "Kaye &Laby Tables of Physical and Chemical Constants," 2.5.8 Refractive index of optical materials, printed Apr. 20, 2016.*

(Continued)

*Primary Examiner* — Tri T Ton
*Assistant Examiner* — Rebecca C Bryant
(74) *Attorney, Agent, or Firm* — McDermott Will & Emery LLP

(57) ABSTRACT

A flow cell includes holding members for holding two ends of a capillary. A refractive index of holding members is 1.31 or less or 1.40 or greater at least in portions through which the holding members make contact with an outer surface of the capillary. A numerical aperture of light for measurement that enters from a light source into the capillary is 0.22 or less so that reflectance of portions through which the holding members make contact with the capillary is constant even when sample liquid that flows through the capillary is converted to water and acetonitrile.

6 Claims, 3 Drawing Sheets

(56) References Cited

U.S. PATENT DOCUMENTS 7,914,852 B2 * 3/2011 Belz et al. .................. 427/379

FOREIGN PATENT DOCUMENTS

| JP | 2002-536673 A | 10/2002 |
|---|---|---|
| JP | 2003-315308 A | 11/2003 |
| JP | 3657900 B2 | 6/2005 |
| JP | 3176582 U | 6/2012 |

OTHER PUBLICATIONS

"Refractive INdex of Steel", Filmetrics https://www.filmetrics.com/refractive-index-database/Stainless+Steel, printed Oct. 26, 2018.*
"Optical Constants of Cu—Zn," https://refractiveindex.info/?shelf=other&book=Cu-Zn&p.=Querry-Cu70Zn30, printed on Oct. 26, 2018.*
Tsunoda et al., "Distribution and Pathway of Source Light in Long Capillary Cell with the Use of Successive Total Reflection at Outer Cell Surface", The Chemical Society of Japan, 1989, (2), pp. 233-236.
Notiifcation of Reasons for Refusal Japanese Patent Application No. 2012-182535 dated Sep. 1, 2015 with English translation.
Akira Kaito et al., "Rolling and drawing-out of a polyether ether ketone (PEEK) sheet", Japanese Journal of Polymer Science and Technology, 1991, vol. 48, No. 11, pp. 663-670—with English Abstract.

* cited by examiner

FLOW CELL

This application claims priority to Japanese Patent Application No. 2012-182535 filed on Aug. 1, 2012, the entire contents of which are incorporated herein by reference.

TECHNICAL FIELD

The present invention relates to a flow cell for allowing a liquid to be measured to flow when, for example, the absorbance of the liquid is measured.

BACKGROUND ART

In an absorbance detector used for a liquid chromatograph or the like, a container that is referred to as cell is irradiated with light for measurement from a light source in such a state that the container is filled in with a liquid to be measured (hereinafter referred to as sample liquid) or the liquid continuously flows through the container so that the intensity of light that has transmitted through the sample liquid is detected, and thus, the absorbance for each wavelength thereof is found. In order to measure a microscopic amount of sample liquid with a high level of sensitivity, it is necessary for the cross-section of the cell to be small and for the length of the optical path to be long. Therefore, a conventional cell that is referred to as light guide cell or the like has been put into practice, where a linear capillary is used as the cell in such a manner that light enters through one end side of the capillary in the direction in which the capillary extends so as to be totally reflected from the outer or inner wall of the capillary and transmitted to the other end side of the capillary (see Non-Patent Document 1 and Patent Documents 1 to 3).

As a flow cell for allowing light to be totally reflected from the outer wall of the capillary and be transmitted, a flow cell where fused quartz is used for the capillary so that light is totally reflected from the interface between the quartz of the outer wall and air has been known (see Patent Document 1).

As a flow cell for allowing light to be totally reflected from the inner wall of the capillary and be transmitted, a flow cell where the capillary of which the inner wall is coated with Teflon (registered trademark) AF has been known (see Patent Document 2).

Light waveguides, such as optical fibers, are often used to allow light for measurement to be emitted from the light source and enter into the capillary.

PRIOR ART DOCUMENTS

Patent Documents

Patent Document 1: U.S. Pat. No. 4,477,186
Patent Document 2: Japanese Translation of International Unexamined Patent Publication 2002-536673
Patent Document 3: Japanese Patent No. 3657900

Non-Patent Document

Non-Patent Document 1: "Distribution and Optical Path for Light from a Light Source in a Capillary Cell with a Long Optical Path Using Total Reflection from the Outer Wall of the Cell" (Kinichi Sumida et al., Nippon Kagaku Kaishi, 1989(2), pp. 233-236, 1989)

SUMMARY OF THE INVENTION

Problem to be Solved by the Invention

In the case where light waveguides, such as optical fibers, are used to introduce light into or to lead light out from a flow cell using a capillary, sometimes the amount of light is greatly reduced because of the coupling loss or the mismatching of the transmission NA (numerical aperture). Therefore, it is desirable for light for measurement to be directly condensed at the end through which light is introduced into the capillary and to pass through the capillary so as to emit as it is from the end from which the light is led out of the capillary. In some cases, however, this structure increases the problem shown in the following.

In an absorbance detector where a flow cell through which a sample liquid flows is used as a light guide cell for leading the light for measurement in the direction in which the sample liquid flows, the amount of light that transmits through the cell changes depending on the refractive index of the sample liquid, and thus, the baseline of the measurement data fluctuates. This phenomenon is referred to as the photorefractive effect.

In the above-described structure of a cell where light for measurement is directly condensed at the end through which the light is introduced into the capillary so as to be emitted as it is from the end on the other side from which the light is led out, the reason why there is the photorefractive effect is considered to be the following.

In the above-described cell structure, light hits a member for holding the capillary in a portion where this holding member makes contact with the capillary. It is usually necessary for the two ends of the capillary to be held in such a state that the liquid tightness thereof is maintained, and the capillary is held by the base through ferrules, which are holding members (coupling members) made of a resin, in such a state that these ferrules made of a resin adhere to the outer wall of the capillary at both ends. The reflectance of light in the case where light enters into the interface between these ferrules or other holding members and the outer wall of the capillary is led out using Fresnel's formula. According to Fresnel's formula, the reflectance of the light guide made of the capillary and the sample liquid that flows through the inside thereof changes due to the difference in the refractive index between the sample liquid that flows through the capillary and the holding members that make contact with the capillary. Though no problem arises if the refractive index of the sample liquid is constant, the results of the measurement of the absorbance include a fluctuation of the baseline in the measurement where the refractive index of the sample liquid chronologically changes as in the gradient analysis using a liquid chromatograph, and thus, there is an error in the results of measurement.

Patent Document 3 has a description that relates to the suppression of the photorefractive effect in a cell using Teflon AF. A structure is used for this where a light waveguide for introducing light for measurement into the capillary or for leading light for measurement out from the capillary is inserted through either end of the capillary, and thus, members of which the material is different from that of the center portion of the capillary make contact with the two ends of the capillary, but light does not hit these contact portions. However, this structure is not compatible with the above-described requirements where it is desirable for light for measurement to be directly guided into an end through which light is introduced into the capillary so that the light is directly emitted from the end through which the light is led out of the capillary.

The present invention is provided in view of the above-described circumstances, and an object thereof is to provide a flow cell that is of a type where light for measurement that has entered through one end of the capillary through which a sample liquid flows is reflected from the outer wall of the capillary so as to be emitted from the other end of the capillary. The flow cell makes it possible to carry out a precise measurement of absorbance without a fluctuation in the baseline by suppressing the photorefractive effect, though the flow cell has such a structure that light for measurement directly enters into the capillary through one end and is directly emitted through the other end without detouring around the portions through which the members for holding the two ends of the capillary make contact with the capillary by using a light waveguide.

Means for Solving Problem

In order to achieve the above-described object, the flow cell according to the present invention has: a linear capillary made of glass through which a sample liquid flows; a light introducing member for introducing light for measurement from a light source; and a light leading out member for leading light that has passed through the sample liquid which flows through the capillary into an external detector, where the light introducing member and the light leading out member are provided at the two ends of the capillary, respectively, and each end of the above-described capillary is held liquid tight by a base through a holding member made of a resin, and is characterized in that the refractive index of the above-described holding member made of a resin in a portion that makes contact with the outer surface of the capillary in all or part of a region through which the above-described light for measurement passes through the capillary is 1.31 or less or 1.40 or greater, and the NA of the light for measurement that enters from the above-described light source into the above-described capillary is 0.22 or less (Claim 1).

In the present invention, it is preferable to adopt such a structure that the light introducing member and the light leading out member at the two ends of the above-described capillary are window members, and the light for measurement from the above-described light source is directly introduced into the above-described capillary through the window member on the light introducing side, and the light that has passed through the sample liquid is directly led out from the above-described capillary to the outside through the window member on the light leading out side (Claim 2).

The present invention is based on the following knowledge.

FIG. 1 shows a model of a flow cell in the vicinity of a holding member 2, such as a ferrule, at an end through which light is introduced into the capillary 1.

The outer wall of the capillary 1 made of glass (particularly fused quartz, for example) makes contact with the holding members 2 made of a resin only through the two end portions and with air through the rest of the outer wall. According to the arithmetic operation on the basis of Fresnel's formula, the smaller the refractive index of the holding members 2 that make contact with the capillary 1 is, the higher the reflectance from the interface between the outer wall of the capillary 1 and the holding members 2 is. In the case of the refractive index of the sample liquid>the refractive index of the holding members, some light is totally reflected depending on the angle at which it enters into the interface. When the angle is smaller than the total reflection critical angle $\theta O$, the reflectance suddenly lowers. When it is assumed that a sample liquid A, a sample liquid B and holding members C have such refractive indices as A>C>B, light that is totally reflected at a certain incident angle in a state where the sample liquid A flows through the capillary 1 stops being totally reflected as soon as the sample liquid A is switched to the sample liquid B, and thus, there is a great fluctuation in the amount of transmission light. It can be seen from this that it is a necessary requirement for suppressing the photorefractive effect that the refractive index of the holding members C be greatly different from the refractive index of the sample liquid that is assumed to flow through the capillary 1.

Here, the photorefractive effect in particular becomes a problem. In a liquid chromatograph, water/ACN (acetonitrile) is generally used for the solvent in the gradient analysis. That is to say, the amount of transmission light must be the same, in other words, the reflectance from the outer wall of the capillary must be equal, whether the sample liquid that flows through the capillary 1 be a water solution with a low concentration (refractive index: 1.333) or an acetonitrile solution (refractive index: 1.344).

In the flow cell used for a liquid chromatograph, PFA (copolymer of tetrafluoroethylene and perfluoro (alkyl vinyl ether)) is used for the holding members of the capillary from the point of view of chemical resistance, where the refractive index of PFA is 1.34, which is close to the refractive index of the above-described solution that flows through the capillary in the gradient analysis in the liquid chromatograph, and therefore, the photorefractive effect becomes great.

In light of this point, the present invention is intended to provide a structure where light that has entered under a certain value of the maximum incident NA (numerical aperture) can be guided in such a manner that the reflectance of the light reflected from the interface between the outer wall of the capillary and the holding members is the same or does not have such a difference as to cause a problem in practice whether the sample liquid that flows through the capillary (made of fused quartz) be a water solution with a low concentration or an acetonitrile solution.

In the present invention, the incident NA is 0.22 or less (maximum incident angle $\theta \approx 12.7°$), and the refractive index of the holding member is selected so that the reflectance of the light that has entered at its maximum incident NA from the interface between the outer wall of the capillary and the holding members is the same or does not have such a difference as to cause a problem in practice in a state where a water solution with a low concentration or an acetonitrile solution is flowing as the sample liquid in the capillary.

That is to say, the upper limit of the refractive index of the holding members at the time of total reflection from the interface between the outer wall of the capillary and the holding members in the case where the sample liquid is a water solution with a low concentration is 1.3147 (total reflection even when the refractive index is greater in the case of an acetonitrile solution), and the lower limit of the refractive index where the difference in the reflection between the water solution with a low concentration and an acetonitrile solution is 0.5% or less (change in the absorbance appears to be approximately 2 mAU or less) is 1.3999. The refractive index in a state where water or acetonitrile flows through the capillary when the maximum incident NA is 0.22 is shown in a graph where the lateral axis shows the refractive index of the holding member. Here, the material of the capillary is fused quartz (refractive index: 1.46). When the refractive index of the holding members is 1.3147 or less, light is totally reflected no matter if water or acetonitrile flows. When the refractive index exceeds 1.3147, total reflection is maintained in the case where the sample liquid is acetonitrile, but the reflectance suddenly lowers in the case where the sample liquid is water, and as a result of the two being greatly different in the reflectance, the photorefractive effect becomes great. When the refractive index of the holding members is 1.399 or greater, the reflectance is close to 0 no matter if the sample liquid is acetonitrile or water, and thus, the difference in the reflectance between the two is 0.5% or less, causing no problems in practice.

Accordingly, the refractive index of the holding members that make close contact with the outer wall of the capillary so as to hold the capillary is 1.31 or less or 1.40 or greater, and this setting is combined with the setting of the incident NA to 0.22 or less, and thus, the reflectance of light from the interface between the outer wall of the capillary and the holding members is substantially the same no matter if water, acetonitrile or a mixture of these flows through the capillary as the solvent, and the amount of light that transmits through the capillary containing the sample liquid flowing through the inside does not change due to the photorefractive effect.

In addition, this reflectance from the interface between the outer wall of the capillary and the holding members substantially maintains a constant value even when the refractive index of the sample liquid changes as in the gradient analysis in the liquid chromatograph, and therefore, the light waveguide for introducing light into and leading light out from the capillary is unnecessary, particularly in order to suppress the photorefractive effect, and thus, no problem arises due to the photorefractive effect even when the structure of the invention according to Claim 2, where window members are provided at the two ends of the capillary so that light for measurement is directly introduced into the capillary and is led out directly from the capillary, is adopted.

Effects of the Invention

According to the present invention, the photorefractive effect of the flow cell using a capillary made of glass, such as fused quartz, can be suppressed, and as a result, the baseline of the absorption data does not change even when the type of sample liquid that flows through the inside is changed during the gradient measurement in a liquid chromatograph, and thus, a precise measurement for absorption becomes possible.

In addition, the photorefractive effect can be suppressed as described above in the flow cell having such a structure that the capillary is held by holding members made of a resin, and therefore, it is not necessary to use light waveguides, such as optical fibers, which have a risk of coupling loss or a change in the transmission NA, in order to introduce light into or lead light out from the capillary, and thus, such a structure as in the invention according to Claim 2 that light is directly introduced and led out through window members can be adopted in order to make a more precise measurement for absorbance possible.

PREFERRED EMBODIMENTS OF THE INVENTION

In the following, the preferred embodiments of the present invention are described in reference to the drawings.

Figure 1:
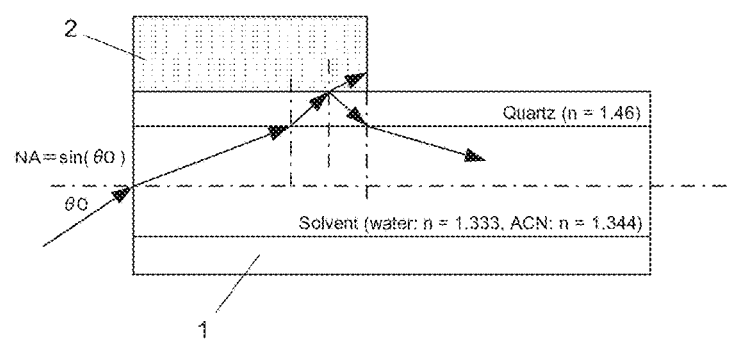
FIG. 1 is a schematic diagram showing a part of a model of a flow cell for illustrating the suppression of the photorefractive effect according to the present invention.
Figure 2:
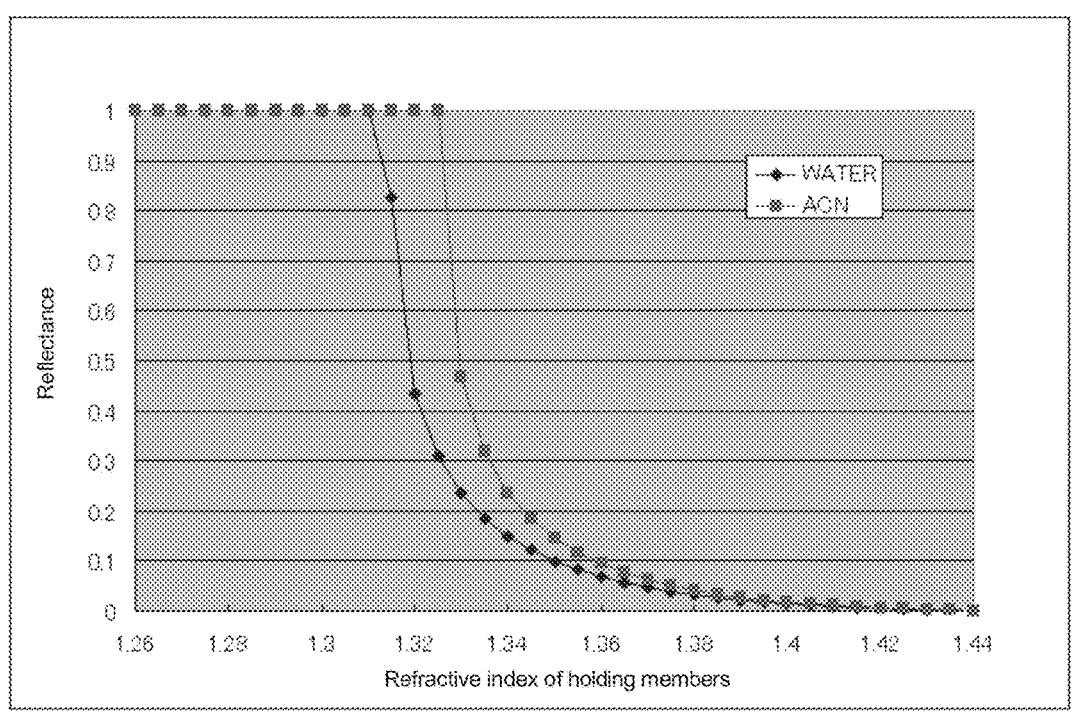
FIG. 2 is a graph showing the reflectance of light with the maximum incident angle when the incident NA is 0.22 for the refractive index of the holding members in both cases where the sample liquid is water and acetonitrile.
Figure 3:
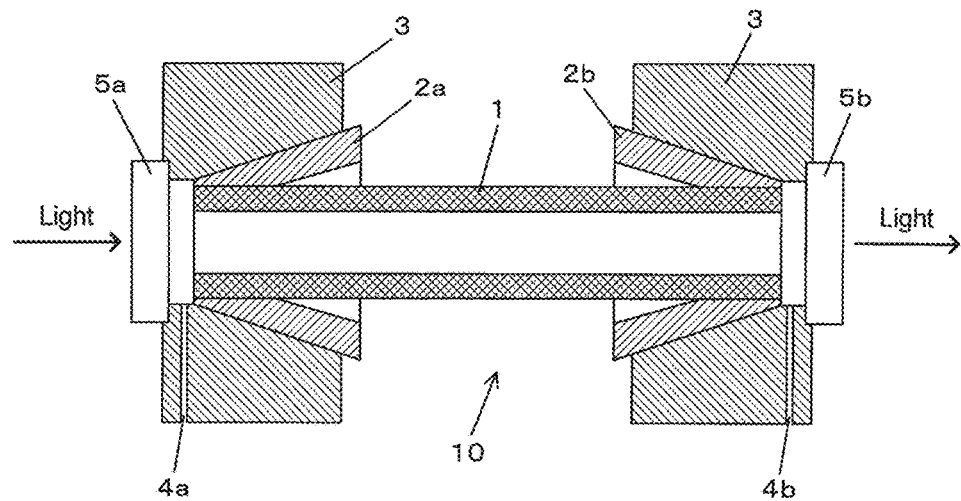
FIG. 3 is a schematic cross-sectional diagram showing the flow cell according to an embodiment of the present invention.

FIG. 3 is a schematic cross-sectional diagram showing a flow cell 10 according to an embodiment of the present invention. The two ends of a capillary 1 made of fused quartz are liquid-tightly connected to a base 3 through holding members 2a, 2b made of a resin, such as ferrules. A liquid introducing path 4a that is connected to one end of the capillary 1 and a liquid leading out path 4b that is connected to the other end of the capillary 1 are formed in the base 3 so that a sample liquid is introduced into the capillary 1 through the liquid introducing path 4a, and the sample liquid that has flown through the capillary 1 is discharged to the outside through the liquid leading out path 4b.

A light introducing window member 5a is provided at one end of the capillary 1 and a light leading out window member 5b is provided at the other end. Light for measurement directly enters into the capillary 1 through the light introducing window member 5a, and the light that has transmitted through the capillary 1 is directly emitted to the outside through the light leading out window member 5b. The forms of the light introducing window member 5a and the light leading out window member 5b are not particularly limited, and they may be lenses or windows with a simple pane, for example.

Figure 4:
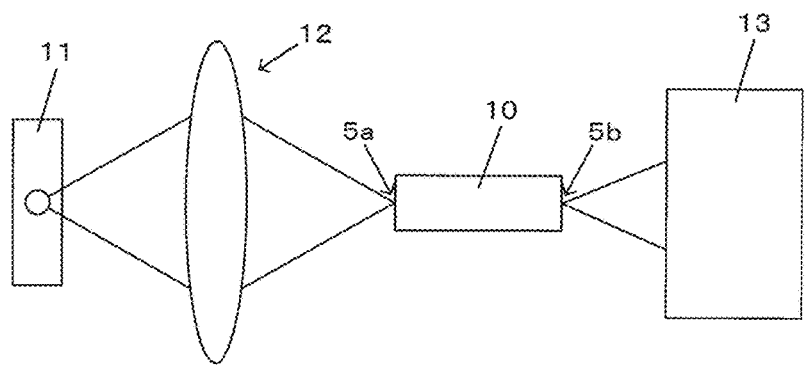
FIG. 4 is a schematic diagram showing the entire structure of the spectral absorbance detector in FIG. 3.

The above-described flow cell 10 is used in the spectral absorbance detector of which the structure in its optical system is illustrated in FIG. 4. The detector illustrated in FIG. 4 detects the absorbance of the sample liquid that has eluded from a column in a liquid chromatograph for each wavelength, for example.

Light from a light source 11 is condensed by a condensing system 12 and guided through the above-described light introducing window member 5a in the flow cell 10. The light that has transmitted through the sample liquid flowing through the flow cell 10, and at the same time is being guided by the flow cell 10, is emitted through the light leading out window member 5b so as to enter into the detection system 13. The detection system 13 is made of a wavelength dispersing element, such as grating and a photodiode array, for example, and this detection system 13 detects the intensity of light that has passed through the sample liquid for each wavelength, and the absorbance for each wavelength of light that has passed through the sample liquid is found from the detection results.

This embodiment is characterized by the refractive index of the material for forming the holding members 2a, 2b which hold the two ends of the capillary 1, where the refractive index is 1.31 or less or 1.40 or greater. It is appropriate to use Teflon AF having a refractive index of 1.29, which is a material having a refractive index of 1.31 or less, as a typical material for the holding members 2a, 2b, taking chemical resistance into consideration, and it is appropriate to use PEEK (registered trademark: Polyether Ether Ketone) having a refractive index of 1.67 as a material having a refractive index of 1.40 or greater.

In addition, the light guided through the light introducing window member 5a in the capillary 1 is controlled by the condensing system 12 so that the incident NA is 0.22 or less. As a result of this setting, the light that has been guided into the capillary 1 is totally reflected from the interface between the outer wall of the capillary 1 and air, and in addition is consistently totally reflected from the interface between the outer wall of the capillary 1 and the holding members 2a, 2b even when the solvent is switched from water to acetonitrile at the time of gradient analysis in the liquid chromatograph in the case where a material having a refractive index of 1.31, for example, Teflon AF, I used for the holding members 2a, 2b of the capillary 1, and thus, the baseline does not fluctuate due to the photorefractive effect.

In the case where a material having a refractive index of 1.40 or greater, for example, PEEK, is used for the holding members 2a, 2b, the light that has been guided into the capillary 1 is totally reflected from the interface between the outer wall of the capillary 1 and air, but the reflectance from the interface between the outer wall of the capillary 1 and the holding members 2a, 2b is consistently close to 0, and the difference in the reflectance between the cases where the solvent is water and acetonitrile is 0.5% or less, which causes no problems in practice even when the solvent is switched from water to acetonitrile during the gradient analysis, and therefore in this case as well, the baseline does not substantially fluctuate due to the photorefractive effect.

Figure 5:
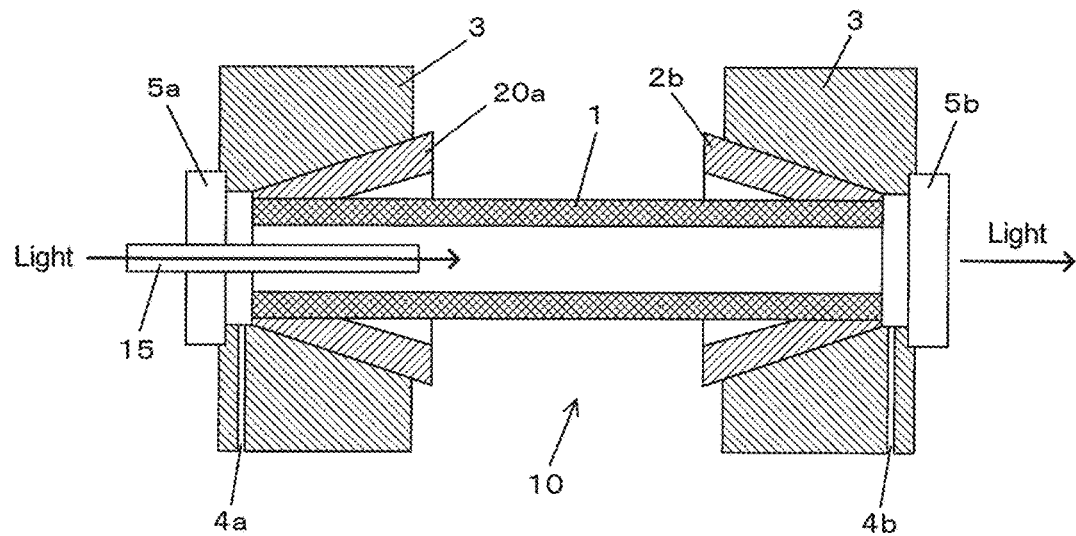
FIG. 5 is a schematic cross-sectional diagram showing a main portion in another embodiment of the present invention.

Though the light introducing window member 5a and the light leading out window member 5b are provided at the two ends of the capillary 1 so that light from the light source 11 is directly introduced into the capillary 1 through the light introducing window member 5a, and at the same time, the light that has transmitted through the sample liquid in the capillary 1 while being guided by the capillary 1 is directly emitted to the outside through the light leading out window member 5b in the above described embodiment, a light waveguide may be used on either the light introducing side or on the light leading out side. FIG. 5 schematically shows an example where a light waveguide 15 is used on the light introducing side, and FIG. 6 schematically shows an example where a light waveguide 16 is used on the light leading out side.

In the example in FIG. 5, which is a case where a light waveguide 15 is used on the light introducing side, the capillary 1 is connected to the base 3 on the light leading out side through a holding member 2b made of a material having a refractive index of 1.31 or less or a refractive index of 1.4 or greater as in the example in FIG. 3, while the holding member 2a on the light introducing side is not hit by the light that has been guided into the capillary 1, and thus, the refractive index thereof may have any value, and accordingly, any material may be used.

Figure 6:
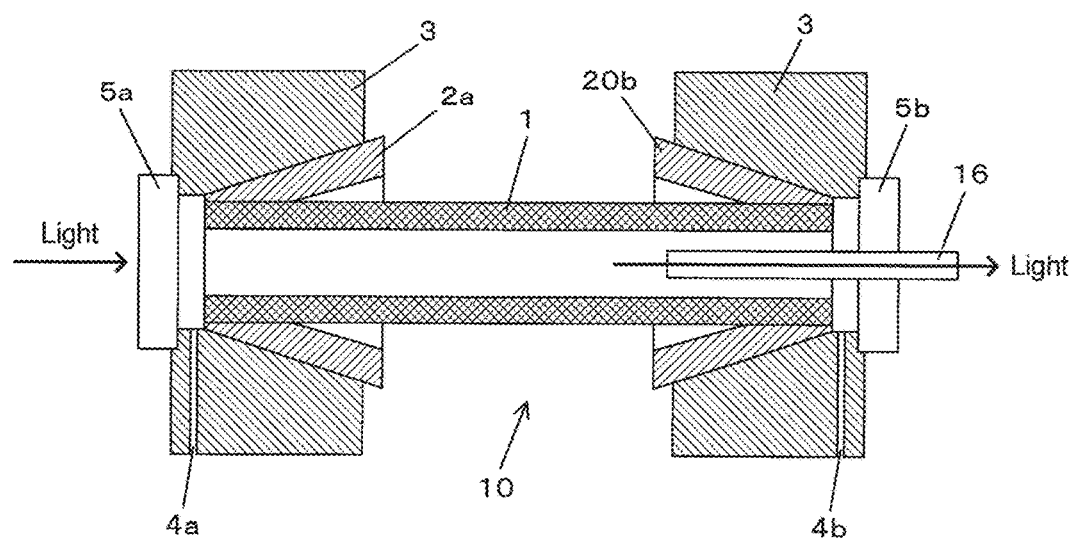
FIG. 6 is a schematic cross-sectional diagram showing a main portion in still another embodiment of the present invention.

In the case where a light waveguide 16 is used on the light leading out side as in FIG. 6, the capillary 1 is connected to the base 3 on the light introducing side through the holding member 20a made of a material having a refractive index of 1.31 or less or a refractive index of 1.4 or greater as in the example in FIG. 3, while the holding member 20b on the light leading out side is not hit by the light that is to be guided to the outside through the light waveguide 16, and thus, the refractive index thereof may have any value, and accordingly, any material may be used.

In the case where a light waveguide is used either on the light introducing side or on the light leading out side, the refractive index of the holding member is 1.31 or less or 1.40 or greater when light hits a holding member in the capillary.

It is also possible in the above-described embodiments that the holding members are made of a material having a refractive index of 1.31 or less or 1.40 or greater, which is uniform throughout its entirety, and the structure, where at least only the portions of the holding members with the surface that makes contact with the capillary are made of a material having a refractive index of 1.31 or less or 1.40 or greater, and the rest of the portions are made of a certain resin, is adopted.

EXPLANATION OF SYMBOLS 1 capillary
2a, 2b holding members
3 base
4a liquid introducing path
4b liquid leading out path
5a light introducing window member
5b light leading out window member
11 light source
12 condensing system
13 detection system
15, 16 light waveguides

The invention claimed is:

1. An absorbance detector for performing a gradient analysis that analyzes a sample liquid being one of 1) water, 2) acetonitrile, or 3) a mixture of the water and the acetonitrile, the absorbance detector comprising:
   a light source;
   a detection system;
   a flow cell comprising:
      a linear capillary having a first end and a second end between which the sample liquid flows, the linear capillary configured to hold the sample liquid;
      a light introducing window, disposed at the first end of the linear capillary, for directly introducing light for measurement from the light source into the linear capillary;
      a light leading out window, disposed at the second end of the linear capillary, for directly leading light that has passed through the sample liquid flowing through the linear capillary into the detection system;
      a first base configured to be connected to the first end of the linear capillary;
      a second base configured to be connected to the second end of the linear capillary;
      a first path disposed between the light introducing window and the first end of the linear capillary, the first path introducing the sample liquid into the first end of the linear capillary;
      a second path disposed between the second end of the linear capillary and the light leading out window, the second path discharging the sample liquid from the second end of the linear capillary;
      a first coupling member for liquid-tightly coupling the first end of the linear capillary to the first base, wherein the first coupling member extends from the first end of the linear capillary towards the second end of the linear capillary, wherein a first portion of the first coupling member contacts an outer surface of the linear capillary, wherein a second portion of the first coupling member does not contact the outer surface of the linear capillary and contacts air, and wherein an interface between the outer surface of the linear capillary and the first coupling member is irradiated with the light for measurement; and a second coupling member for liquid-tightly coupling the second end of the linear capillary to the second base, wherein the second coupling member extends from the second end of the linear capillary towards the first end of the linear capillary, wherein a first portion of the second coupling member contacts the outer surface of the linear capillary, wherein a second portion of the second coupling member does not contact the outer surface of the linear capillary and contacts the air, and wherein an interface between the outer surface of the linear capillary and the second coupling member is irradiated with the light for measurement, wherein at least the first portion of the first coupling member has a refractive index of 1.31 or less or 1.40 or greater and at least the first portion of the second coupling member has a refractive index of 1.31 or less or 1.40 or greater; and a condensing system disposed between the light source and the flow cell such that the light for measurement enters the light introducing window of the flow cell at a maximum incident angle of 12.7 degrees or less to maintain a reflectance of the light for measurement reflecting from an interface between the outer surface of the linear capillary and the first portion of the first coupling member and an interface between the outer surface of the linear capillary and the first portion of the second coupling member regardless of whether the sample liquid is 1) the water, 2) the acetonitrile, or 3) the mixture, wherein the first portion of the first coupling member and the second portion of the first coupling member are disposed on an inner surface of the first coupling member, wherein the inner surface of the first coupling member faces the linear capillary, wherein the first portion of the second coupling member and the second portion of the second coupling member are disposed on an inner surface of the second coupling member, and wherein the inner surface of the second coupling member faces the linear capillary.

2. The flow cell according to claim 1, wherein a path for the light for measurement from said light source propagating in said linear capillary is in line with a path of the sample liquid flowing in said linear capillary.

3. The flow cell according to claim 1, wherein no optical waveguide is disposed in front of the light introducing window.

4. An absorbance detector for performing a gradient analysis that analyzes a sample liquid being one of 1) water, 2) acetonitrile, or 3) a mixture of the water and the acetonitrile, the absorbance detector comprising:
a light source;
a detection system;
a flow cell comprising:
a linear capillary having a first end and a second end between which the sample liquid flows, the linear capillary configured to hold the sample liquid;

a light introducing window, disposed at the first end of the linear capillary, for directly introducing light for measurement from the light source into the linear capillary;

a first base configured to be connected to the first end of the linear capillary;

a second base configured to be connected to the second end of the linear capillary;

a first path disposed between the light introducing window and the first end of the linear capillary, the first path introducing the sample liquid into the first end of the linear capillary;

a second path discharging the sample liquid from the second end of the linear capillary;

a first coupling member for liquid-tightly coupling the first end of the linear capillary to the first base, wherein the first coupling member extends from the first end of the linear capillary towards the second end of the linear capillary, wherein a first portion of the first coupling member contacts an outer surface of the linear capillary, wherein a second portion of the first coupling member does not contact the outer surface of the linear capillary and contacts air, and wherein an interface between the outer surface of the linear capillary and the first coupling member is irradiated with the light for measurement; and a second coupling member for liquid-tightly coupling the second end of the linear capillary to the second base, wherein the second coupling member extends from the second end of the linear capillary towards the first end of the linear capillary, wherein at least a portion of the second coupling member contacts the outer surface of the linear capillary, wherein at least the first portion of the first coupling member has a refractive index of 1.31 or less or 1.40 or greater; and a condensing system disposed between the light source and the flow cell such that the light for measurement enters the light introducing window of the flow cell at a maximum incident angle of 12.7 degrees or less to maintain a reflectance of the light for measurement reflecting from an interface between the outer surface of the linear capillary and the first portion of the first coupling member regardless of whether the sample liquid is 1) the water, 2) the acetonitrile, or 3) the mixture, wherein the first portion of the first coupling member and the second portion of the first coupling member are disposed on an inner surface of the first coupling member, wherein the inner surface of the first coupling member faces the linear capillary, wherein the first portion of the second coupling member and the second portion of the second coupling member are disposed on an inner surface of the second coupling member, and wherein the inner surface of the second coupling member faces the linear capillary.

5. An absorbance detector for performing a gradient analysis that analyzes a sample liquid being one of 1) water, 2) acetonitrile, or 3) a mixture of the water and the acetonitrile, the absorbance detector comprising:
a light source;
a detection system;
a flow cell comprising:

a linear capillary having a first end and a second end between which the sample liquid flows, the linear capillary configured to hold the sample liquid;

a light leading out window, disposed at the second end of the linear capillary, for directly leading light that has passed through the sample liquid flowing through the linear capillary into the detection system;

a first base configured to be connected to the first end of the linear capillary;

a second base configured to be connected to the second end of the linear capillary;

a first path introducing the sample liquid into the first end of the linear capillary;

a second path disposed between the second end of the linear capillary and the light leading out window, the second path discharging the sample liquid from the second end of the linear capillary;

a first coupling member for liquid-tightly coupling the first end of the linear capillary to the first base, wherein the first coupling member extends from the first end of the linear capillary towards the second end of the linear capillary, wherein at least a portion of the first coupling member contacts an outer surface of the linear capillary; and a second coupling member for liquid-tightly coupling the second end of the linear capillary to the second base, wherein the second coupling member extends from the second end of the linear capillary towards the first end of the linear capillary, wherein a first portion of the second coupling member contacts the outer surface of the linear capillary, wherein a second portion of the second coupling member does not contact the outer surface of the linear capillary and contacts air, and wherein an interface between the outer surface of the linear capillary and the second coupling member is irradiated with the light for measurement, wherein at least the first portion of the second coupling member has a refractive index of 1.31 or less or 1.40 or greater; and a condensing system disposed between the light source and the flow cell such that the light for measurement enters the light introducing window of the flow cell at a maximum incident angle of 12.7 degrees or less to maintain a reflectance of the light for measurement reflecting from an interface between the outer surface of the linear capillary and the first portion of the second coupling member regardless of whether the sample liquid is 1) the water, 2) the acetonitrile, or 3) the mixture, wherein the first portion of the first coupling member and the second portion of the first coupling member are disposed on an inner surface of the first coupling member, wherein the inner surface of the first coupling member faces the linear capillary, wherein the first portion of the second coupling member and the second portion of the second coupling member are disposed on an inner surface of the second coupling member, and wherein the inner surface of the second coupling member faces the linear capillary.

6. The flow cell according to claim 1, wherein the first coupling member comprises a first tapered structure that tapers towards the first end of the linear capillary, and wherein the second coupling member comprises a second tapered structure that tapers towards the second end of the linear capillary.

* * * * *